US00PP11778P2

(12) United States Plant Patent
Jepsen

(10) Patent No.: US PP11,778 P2
(45) Date of Patent: Feb. 13, 2001

(54) KALANCHOE PLANT NAMED 'JEPLINA'

(75) Inventor: Knud Jepsen, Hinnerup (DK)

(73) Assignee: Knud Jepsen A/S, Hinnerup (DK)

( * ) Notice: Under 35 U.S.C. 154(b), the term of this patent shall be extended for 0 days.

(21) Appl. No.: 09/334,027

(22) Filed: Jun. 15, 1999

(51) Int. Cl.[7] ..... A01H 5/00
(52) U.S. Cl. ..... Plt./338

(58) Field of Search ..... Plt./338, 336, 335

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Kalanchoe plant named 'Jeplina', characterized by its numerous large yellow flowers; upright and compact plant habit; small dark green crenate leaves; and good postproduction longevity.

2 Drawing Sheets

BACKGROUND OF THE INVENTION

The present invention relates to a new and distinct cultivar of Kalanchoe plant, botanically known as *Kalanchoe blossfeldiana*, and hereinafter referred to by the cultivar name Jeplina.

The new Kalanchoe is a product of a planned breeding program conducted by the Inventor in Hinnerup, Denmark. The objective of the breeding program was to create new freely-flowering Kalanchoe cultivars with compact plant habit, small leaves and large flowers.

The new Kalanchoe originated from a cross made by the Inventor of an unnamed proprietary seedling selection of *Kalanchoe blossfeldiana* as the male, or pollen, parent with the *Kalanchoe blossfeldiana* proprietary selection identified as KJ 92-066 as the female or seed parent. The cultivar Jeplina was discovered and selected by the Inventor as a flowering plant within the progeny of the stated cross in a controlled environment in Hinnerup, Denmark.

Asexual reproduction of the new Kalanchoe by terminal cuttings taken at Hinnerup, Denmark, has shown that the unique features of this new Kalanchoe are stable and reproduced true to type in successive generations.

BRIEF SUMMARY OF THE INVENTION

The cultivar Jeplina has not been observed under all possible environmental conditions. The phenotype may vary somewhat with variations in environment such as temperature, daylength and light intensity, without, however, any variance in genotype.

The following observations, measurements and comparisons describe plants grown in Hinnerup, Denmark, under commercial practice in a glass-covered greenhouse.

The following traits have been repeatedly observed and are determined to be the unique characteristics of 'Jeplina'. These characteristics in combination distinguish 'Jeplina' as a new and distinct cultivar:

1. Very freely flowering; numerous large yellow flowers.
2. Upright and compact plant habit.
3. Small dark green crenate leaves.
4. Good postproduction longevity.

BRIEF DESCRIPTION OF THE PHOTOGRAPHS

The accompanying colored photographs illustrate the overall appearance of the new Kalanchoe, showing the colors as true as it is reasonably possible to obtain in colored reproductions of this type. The photographs were taken under diffuse natural light conditions on an overcast day with electronic flash at approximately noon in Hinnerup, Denmark.

The photograph on the first sheet comprises a side perspective view of a typical potted plant of 'Jeplina'.

The photograph at the top of the second sheet comprises a top perspective view of a typical potted plant of 'Jeplina' showing the flowers and foliage.

The photograph at the bottom of the second sheet is a close-up view of the following: side perspective view of a typical flowering cyme; top perspective view of a typical flowering cyme; and immature (top) and fully expanded leaves (bottom). Flower and foliage colors in the photographs may appear different from the actual colors due to light reflectance. Plants depicted in the photographs were of the same age and grown under the same environmental conditions as described in the detailed botanical description.

DETAILED BOTANICAL DESCRIPTION

In the following description, color references are made to The Royal Horticultural Society Colour Chart except where general terms of ordinary dictionary significance are used. The plants described were about 13 to 15 weeks of age from propagation of unrooted cuttings, were grown at an average temperature of 20 degrees Celsius in glass-covered greenhouses and had been pinched.

Botanical classification: *Kalanchoe blossfeldiana* cultivar Jeplina.

Parentage:

*Male or pollen parent.*—Unnamed proprietary seedling selection of *Kalanchoe blossfeldiana.*

*Female or seed parent.*—*Kalanchoe blossfeldiana* proprietary selection identified as KJ 92-066.

Propagation:

*Type cutting.*—Terminal cuttings.

*Time to initiate roots.*—About 14 days.

*Rooting habit.*—Numerous, fine, fibrous, and well-branched.

Plant description:

*Form.*—Upright and compact plant habit with numerous compound cymes; very freely flowering. Actual plant shape will depend on whether or not plants are pinched (apical terminals removed). Short internodes; upright flowering stems. Finished plant size is appropriate for one plant per 9 to 10-cm container or three plants per 13-cm container.

*Branching habit.*—Freely branching. Pinching (removal of terminal apex) is not required but will enhance lateral branch development.

*Plant height at flowering.*—About 25 cm.

*Plant diameter at flowering.*—About 24 cm.

*Foliage description.*—Leaves simple, opposite, generally symmetrical. Size: Leaf size is reduced after floral induction. Vegetative plants: Length: About 11 cm. Width: About 8.5 cm. Reproductive plants: Length: About 7 cm. Width: About 4.5 cm. Shape: Ovate to elliptic. Apex: Obtuse. Base: Cuneate to obtuse. Margin: Crenate. Texture: Leathery, glabrous, and succulent. Color: Young foliage, upper surface: 137A. Young foliage, lower surface: 138B. Mature foliage, upper surface: 147A. Mature foliage, lower surface: 147B.

Flower description:

*Flower type and habit.*—Single flowers arranged in compound dichasial cymes that arise from leaf axils. Freely flowering. Flowers persistent.

*Natural flowering season.*—Late autumn/winter/early spring; flower initiation and development can be induced under short day/long night conditions.

*Inflorescences borne.*—Above foliage, arising from leaf axils.

*Time to flower.*—In the summer with 20° C. growing temperatures, about 9.5 weeks of short day/long night conditions are required to produce flowering plants. During the winter with supplemental lighting and 20° C. growing temperatures, about 11.5 weeks or short day/long night conditions are required to produce flowering plants. Time to flower is primarily dependent upon temperature and light intensity.

*Flower opening.*—First flower open is the terminal flower at the main axis and is followed by the opening of the terminal flowers of the side branches of the inflorescence. About 1.5 weeks after the first flower has opened, 50% of the remaining flowers are open.

*Flower diameter.*—About 2 cm.

*Quantity.*—Very freely flowering, at least 250 flowers per plant.

*Flower buds.*—Shape: Narrowly oblong. Length: About 1.5 cm. Width: About 4 mm. Color: Dusty yellow, 12B.

*Petals.*—Quantity: Four fused at base. Length: About 7 mm. Shape: Round obovate. Apex: Cuspidate. Margin: Entire. Texture: Glabrous, smooth and satiny. Color: Mature, upper surface: 12B. Mature, lower surface: 12C.

*Reproductive organs.*—Stamens: Stamen number: Eight. Anther shape: Slightly oblong. Filament color: Yellow green. Pollen color: Yellow. Pistils: Pistil number: Four. Style color: Greenish. Stigma shape: Round. Ovaries: Hypogenous and four-celled. Ovary size: 6 mm by 1 mm. Ovary color: Light green.

Disease resistance: Resistance to known Kalanchoe diseases has not been observed to date under commercial practice.

Seed production: Seed production has not been observed.

It is claimed:

1. A new and distinct cultivar of Kalanchoe plant named 'Jeplina', as illustrated and described.

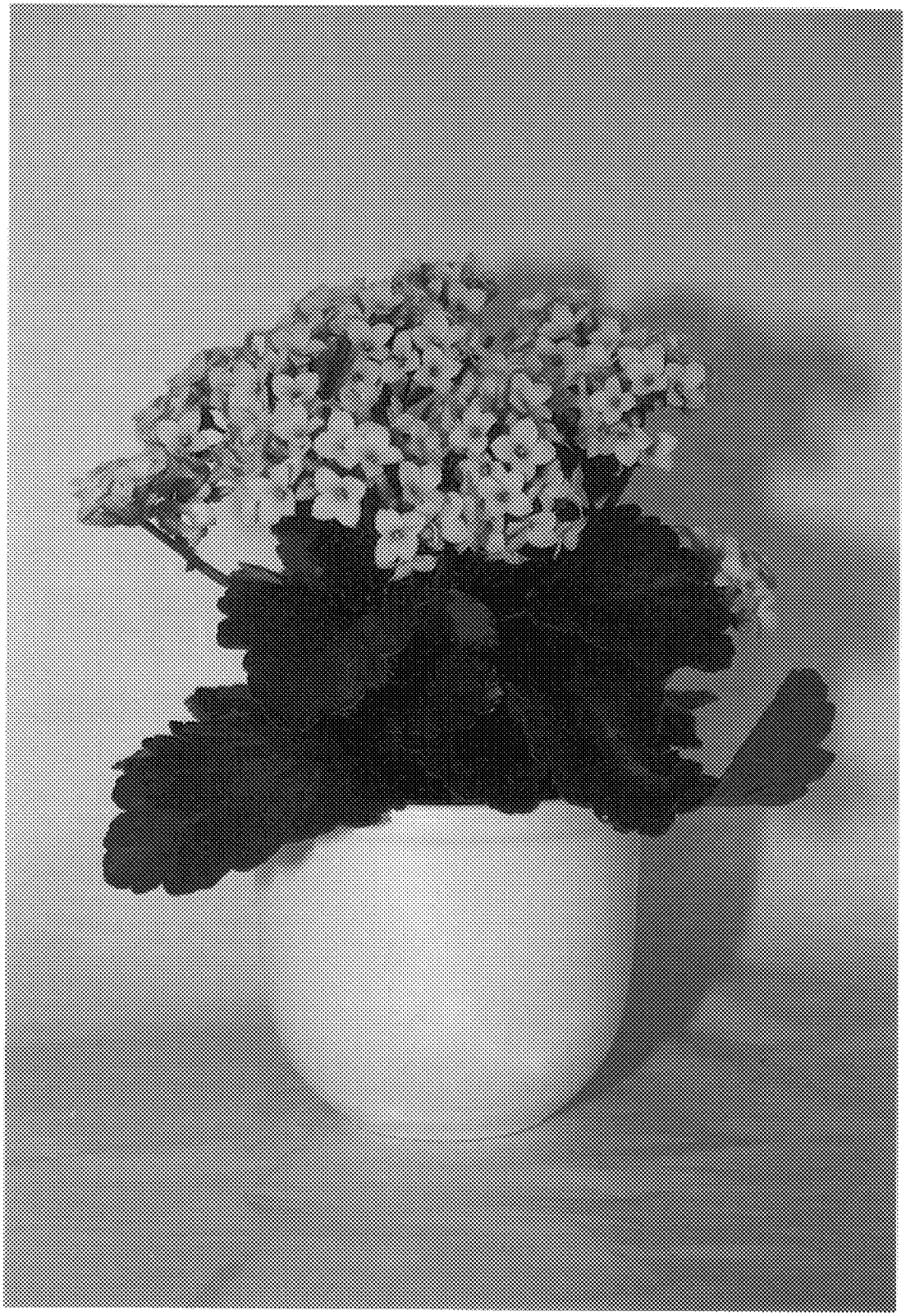

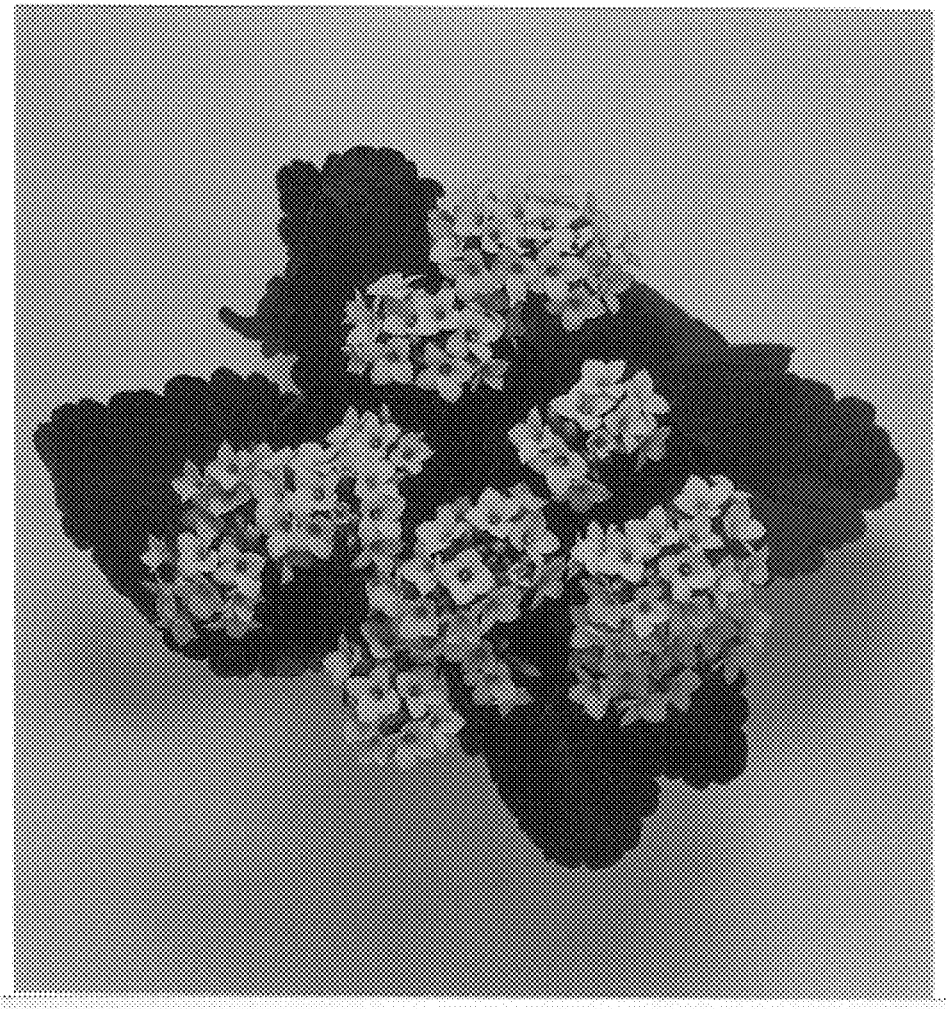
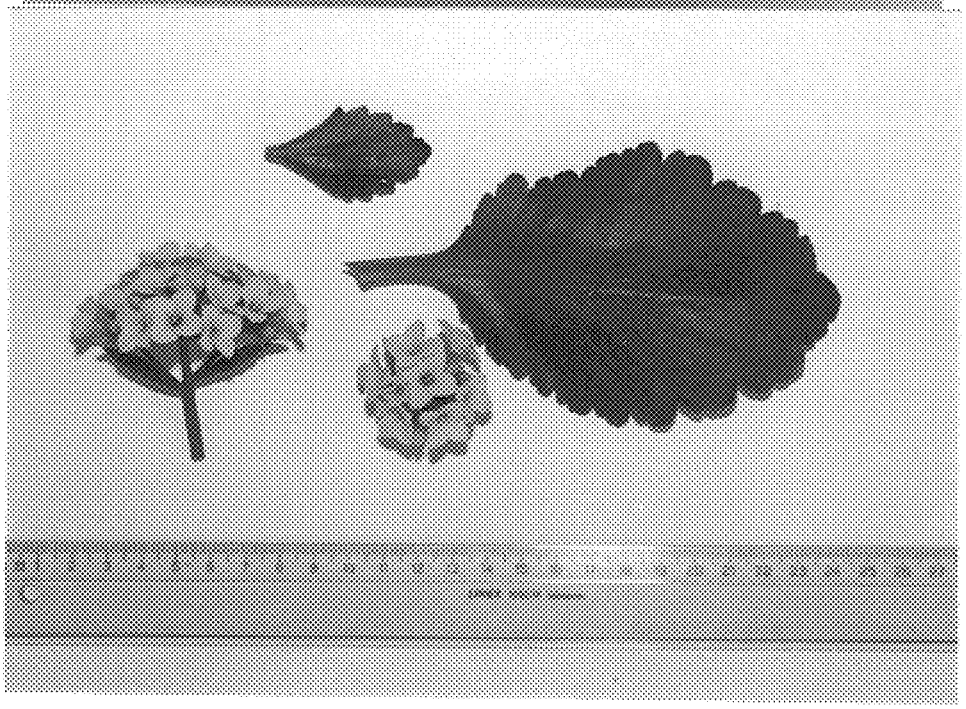

* * * * *